United States Patent
Tweedle

[19]

[11] Patent Number: 6,164,279
[45] Date of Patent: Dec. 26, 2000

[54] WOUND PROTECTING DEVICE

[76] Inventor: Jack A. Tweedle, 303 Shady La., Shorewood, Ill. 60435

[21] Appl. No.: 09/312,783

[22] Filed: May 17, 1999

Related U.S. Application Data

[62] Division of application No. 08/971,431, Nov. 17, 1997.

[51] Int. Cl.$^7$ ........................................................ A61F 13/00
[52] U.S. Cl. .............................................. 128/888; 602/42
[58] Field of Search ........................ 128/846, 877, 128/878, 879, 888, 889; 602/41–48

[56] References Cited

U.S. PATENT DOCUMENTS

| | | |
|---|---|---|
| 1,319,299 | 10/1919 | Meehan ................................ 128/888 |
| 2,367,690 | 1/1945 | Purdy . |
| 2,520,436 | 8/1950 | Russell . |
| 2,785,677 | 3/1957 | Stumpf ................................ 128/888 |
| 3,026,874 | 3/1962 | Stevens . |
| 3,528,416 | 9/1970 | Chamberlain . |
| 3,976,066 | 8/1976 | McCartney . |
| 4,000,737 | 1/1977 | Horn . |
| 4,023,569 | 5/1977 | Warnecke et al. . |
| 4,155,360 | 5/1979 | Erickson . |
| 4,159,021 | 6/1979 | Casburn . |
| 4,212,296 | 7/1980 | Schaar ................................ 128/888 |
| 4,226,232 | 10/1980 | Spence ................................. 602/48 |
| 5,682,905 | 11/1997 | Grant ................................. 128/888 |

Primary Examiner—Michael A. Brown
Attorney, Agent, or Firm—Imre Balogh

[57] ABSTRACT

Device for protecting large wounds, such as surgical incisions, from the environment. The device contains a semi-rigid, flexible plate with attaching means which direct environmental pressures away from the wound.

17 Claims, 7 Drawing Sheets

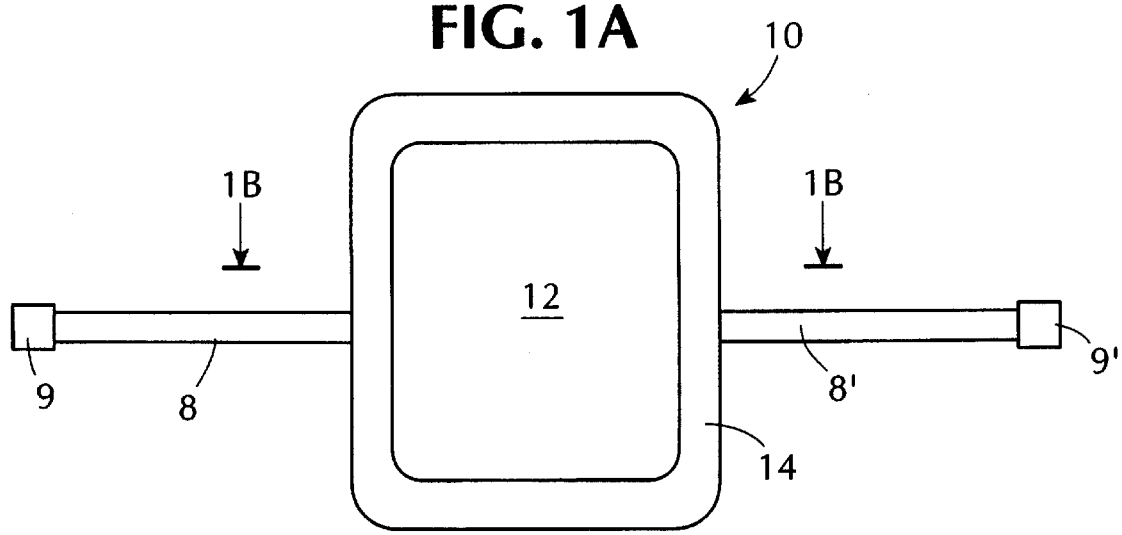
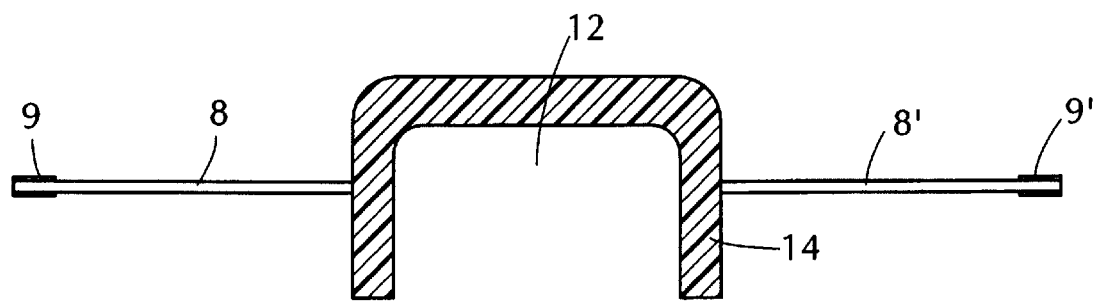
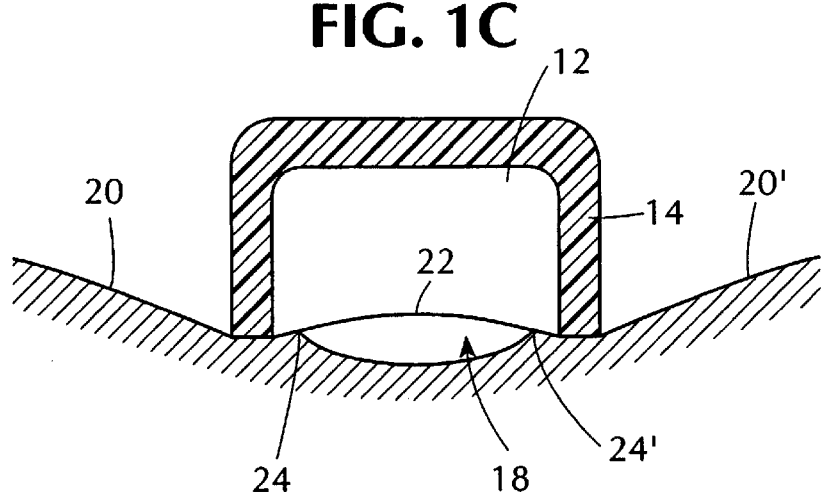

WOUND PROTECTING DEVICE

This application is a divisional of Application Ser. No. 08/971,431 filed on Nov. 17, 1997.

BACKGROUND OF THE INVENTION

1. Field of the Invention

The present invention relates to medical devices designed to protect wounds of patients against outside forces accidentally coming in contact with the wounds. More particularly, the invention relates to dressings which protect incision wounds during the healing process.

2. Reported Developments

Serious skin wounds resulting from surgical incisions are sensitive to excessive pressure such as that produced by clothing worn by the patient. Such pressure is particularly dangerous when the wound is in an area where tight fitting clothing is often worn. Modern wound closing techniques are strong enough to withstand some light pressure on a bandaged wound if the pressure is evenly distributed, but strong and/or uneven pressure can cause pain, break the healing scab, pull or even break the sutures. An example of the later undesirable situation is the waistband of a pair of trousers running perpendicular to a vertical incision wound resulting from abdominal surgery.

In very serious, deep and irregular wounds such as large burned skin areas, or with surgical incisions pressure is so undesirable that protective devices have been invented by the prior art to keep clothing and foreign objects away from the wounded area. These devices are of two types, called herein Type I and Type II.

In Type I the devices contain rigid or semi-rigid rods or strips with supports that lift the rods or strips away from the wound in a direction perpendicular to the body surface. Examples are found in U.S. Pat. Nos. 3,976,066; 4,159,021; 4,000,737; and 2,520,436. These devices create an air pocket between the wound and the clothing, and are held in place by flexible straps or adhesive applied to the supports. The common characteristic of these devices is the presence of flat, foot-like endings to the strips or rods which transfer the pressure, for example from clothing or a sharp blow, from directionally perpendicular to the wound to the skin surrounding the wound at the fixed points where the feet contact the skin around the wound. This protects the wound from a direct, uneven pressure, reducing the magnitude of the pressure by dividing that pressure into the number of foot-like endings, and dissipating the pressure by transferring it to several points in the skin, more or less evenly around the wound.

Type II devices are found for example in U.S. Pat. Nos. 3,026,874; 2,367,690; 4,023,569; 2,663,020; 3,528,416; and 1,319,299. Here the pressure is again transferred away from the wound by creating an air space over the wound. Here the absorbed pressure is then further reduced in magnitude per skin contact point over Type I devices because pressure is transferred to more area of the skin in a continuous line or lines, for example a ring, or square surrounding the wound. In both types of devices, the attempt is to change perpendicular, uneven pressure directed at the wound to more even pressure of a lower magnitude by spreading it over a larger area and redirect it to the skin surrounding the wound.

SUMMARY OF THE INVENTION

The present invention provides devices for protecting wounds, especially large wounds such as incision wounds and wounds requiring stitching. More particularly, the device of the present invention is directed to the protection of large wounds on the body portion of a patient where clothing rubs against the wound and disrupts the healing process. Wounds on the waist, back, abdomen and breast areas are especially susceptible to such undesirable forces and pressures originating from the clothes of the patient or from other environmental objects accidentally coming into contact with the wounds.

The main object of the present invention is to prevent environmental pressures reaching the wound by the presence of a flexible but semi-rigid sheet or plate which directs the pressures away from the wound and dissipates them onto the intact surface of the skin.

In addition, the design of the devices insures that the dissipated pressures will not exert a wound opening force on the surrounding skin but preferably will exert a wound closing force so that the healing process is not disrupted.

The flexible, semi-rigid sheet or plate is equipped with attaching means with which the device is held in place. The attaching means are flexible allowing movement of the sheet or plate over the wound. To soften contact between the sheet or plate and the wound, the sheet or plate is covered on the skin facing side with a soft woven or non-woven fabric, such as medical gauze, which gauze may be optionally coated with a pharmaceutical which aids in wound healing or comfort.

BRIEF DESCRIPTION OF THE DRAWINGS

FIG. 1A is a top plan view of a prior art wound dressing;

FIG. 1B is a cross-sectional view of the prior art wound dressing of FIG. 1A taken along the line 1B—1B;

FIG. 1C is a cross-sectional view of the prior art wound dressing shown in cross-sectional view in FIG. 1B placed on the wound of a patient;

DETAILED DESCRIPTION OF THE DRAWINGS

Figure 2A:
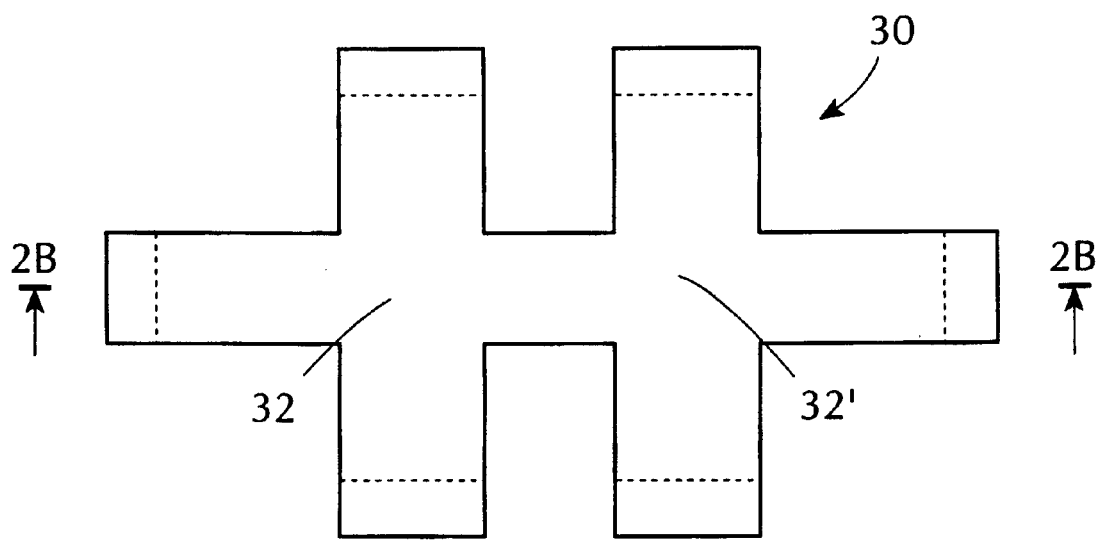
FIG. 2A is a top plan view of another type of a prior art wound dressing.

FIG. 1A is a top plan view of a generalized prior art wound dressing device 10, having a top, wound covering surface 12, and marginal rim area 14 which typically carries a pressure sensitive adhesive or optional straps 8 and 8' with buckles or adhesive areas 9 and 9' for attachment of the wound dressing device 10 to the skin around the wound of the patient.

FIG. 1B is cross-sectional view of FIG. 1A, taken along the line 1B—1B of FIG. 1A.

FIG. 1C is a cross-sectional view of FIG. 1A taken along the line 1B—1B of FIG. 1A placed on the wound designated generally as 18 of the patient and around the adjacent contiguous skin 20 and 20' of the patient. Typically, wound 18 consists of a central portion 22, such as caused by a surgical incision or by a sharp object accidentally penetrating the skin, and immediate wound area surrounding the center portion of the wound designated by 24 and 24'.

This prior art wound dressing handles the force exerted thereon by external objects, such as clothing rubbing against the dressing, by directing the downward pressure towards marginal rim area 14 around the wound and stretching the center portion of wound area 22 thus tending to open the wound such as made by an incision. Such stretching, if its minor, interferes with the healing process, while excessive stretching results in total reopening of the wound necessitating re-stitching the wound.

Figure 2B:
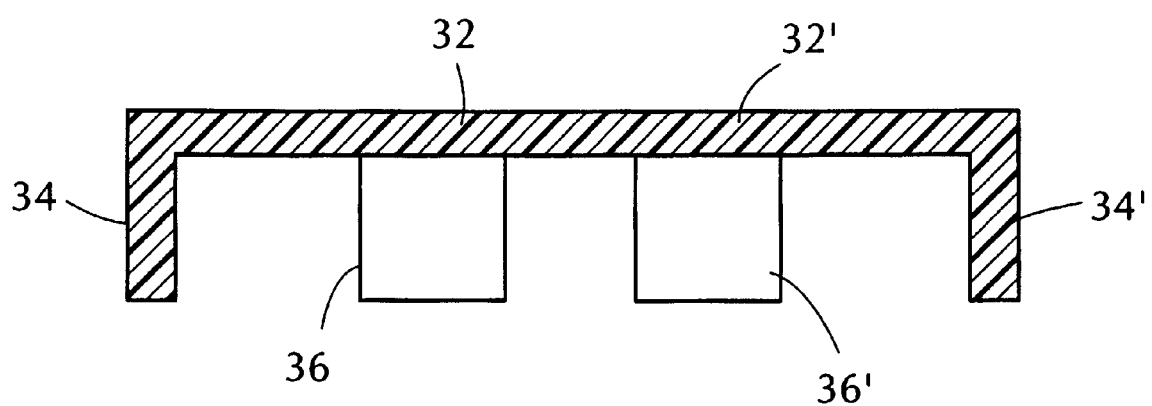
FIG. 2B is a cross-sectional view of the prior art wound dressing taken along the line 2B—2B of FIG. 2A.
Figure 3A:
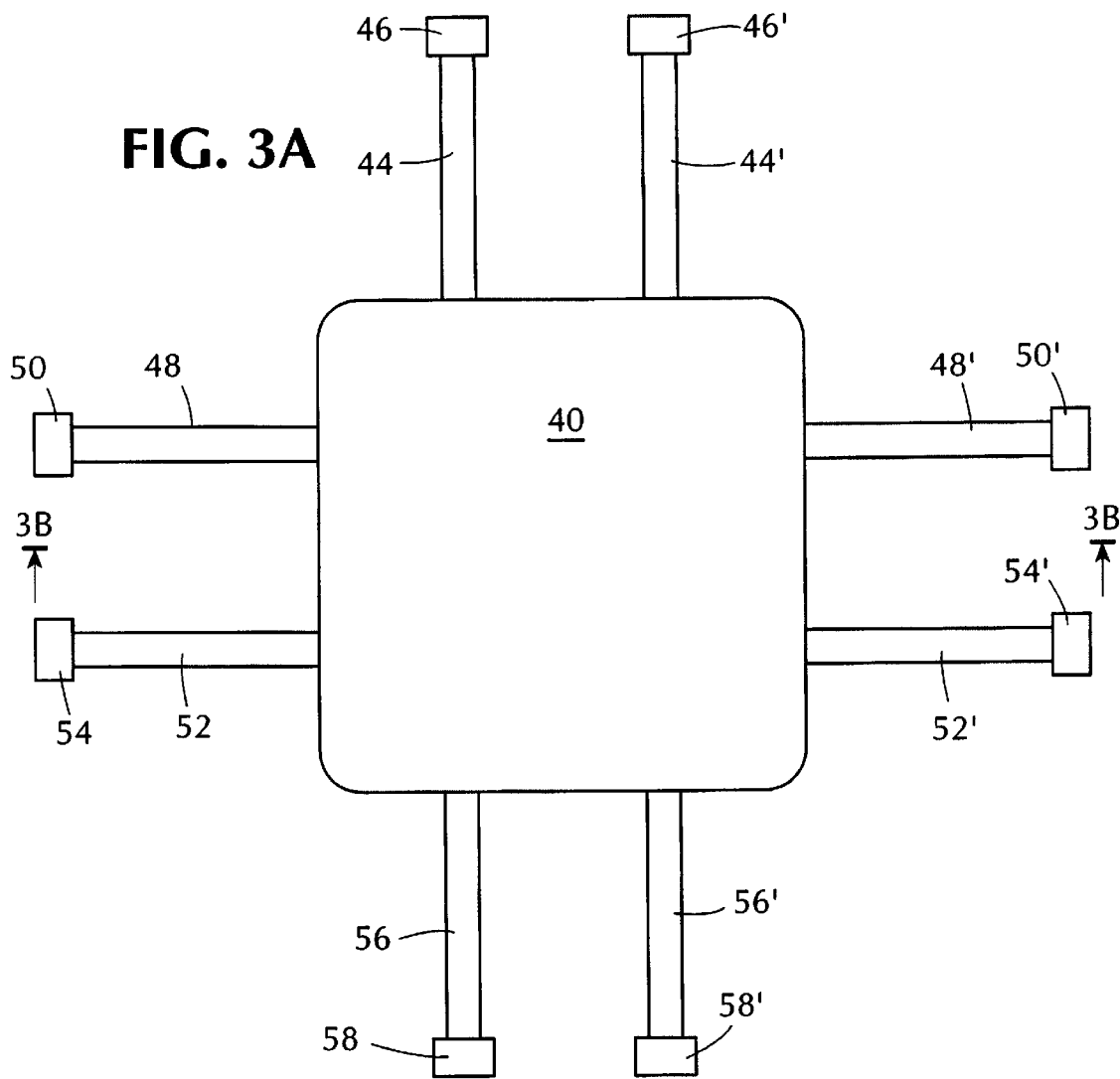
FIG. 3A is a top plan view of one embodiment of the wound dressing of the present invention.
Figure 3B:
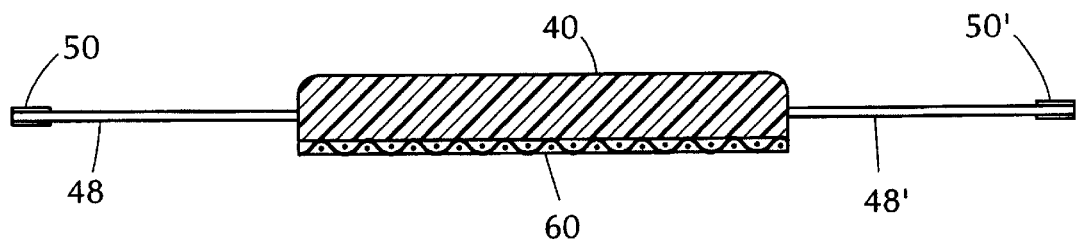
FIG. 3B is a cross-sectional view of the embodiment taken along the line of 3B—3B of FIG. 3A.

FIGS. 2A and 2B illustrate another type of prior art dressings in which external forces exerted on the dressing are concentrated towards narrow marginal areas where: top portion of the dressing 30 is designated by 32 and 32'; marginal rim portions 34, 34', 36 and 36' typically carrying a pressure sensitive adhesive thereon by which the dressing 30 is attached to the skin around the wound. The dressing takes an external force exerted thereon and concentrates the force into the narrow marginal rim portions. While on appearance this type of dressing should reduce the stretching forces exerted on the wound, it still allows opening of the wound and thereby disturbing the healing process FIGS. 3A and 3B show one embodiment of the present invention in top and cross-sectional views. In this embodiment the top of the dressing is designated by the numeral 40 showing a generally rectangular configuration. However, other configurations, such as circular, oval or strip-like configurations may also be included in this embodiment. The underlying surface facing the wound is preferably covered with a soft medical gauze 60 optionally impregnated with a pharmaceutical. The numerals 44, 44', 48, 48', 52, 52', 56 and 56' denote straps which are preferably coated with a pressure sensitive adhesive for attachment of the dressing to the patient's skin. Alternatively, the straps may be equipped with Velcro fasteners or buckles designated as 46, 46', 50, 50', 54, 54', 58 and 58'. The Velcro fasteners of buckles are preferably used when the dressing is placed on areas of the body where the straps may be wrapped around the body, such as the waist area. Alternatively, the right pressure of clothing may be used to hold the device in place around the waist area without straps.

In use, forces exerted on the semi-rigid, flexible dressing are spread equally over the area of the wound and its surroundings which prevent the presence of wound opening forces. The dressing is not spaced from the wound and external forces exerted on the wound will be absorbed by the semi-rigid, flexible dressing and evenly distributed to the whole skin area around the wound unlike the prior art dressings which distribute the forces unevenly at concentrated points around the wound thereby stretching the skin at and adjacent to the wound. The thickness of the dressing is dependent on the material used. For flexible metal, such as aluminum, the dressing should be from about 1/64 to about 1/16 inch. When the dressing is made of plastics, the dressing must be slightly thicker: of from about 1/32 to about 1/4 inches, preferably of from about 1/16 to about 3/32 inches for polypropylene or polyethylene plastics.

Figure 4A:
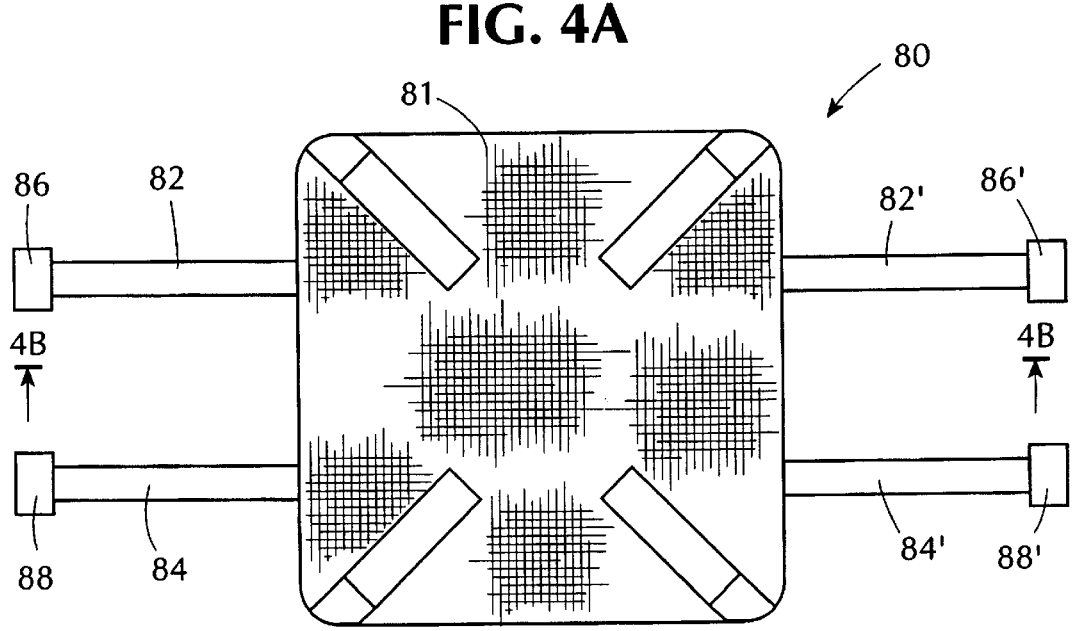
FIG. 4A is a top plan view of another embodiment of the wound dressing of the present invention.
Figure 4B:
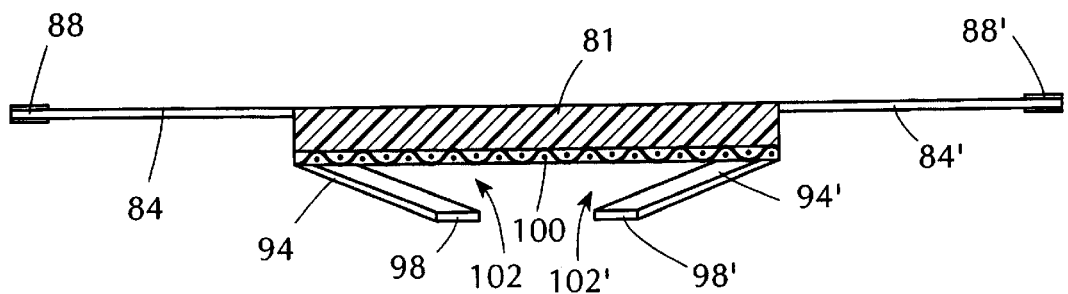
FIG. 4B is a cross-sectional view of the embodiment taken along the line 4B—4B of FIG. 4A.

FIGS. 4A and 4B show another embodiment of the present invention comprising acute angled feet on flexible hinges attached to the body of the dressing. FIG. 4A shows the top plan view of the dressing and FIG. 4B shows a sectional view thereof taken along the line 4B—4B of FIG. 1A. Dressing 80 comprises: a top portion 81 made of a flat, flexible plastic or thin metal plate, optionally covered on the wound contacting side thereof with a soft textile material 100 such as surgical gauze optionally impregnated with a pharmaceutical; flat or round bottomed feet designated 98, 98' attached to the top portion 81 of the dressing 80 with hinges, 94, 94' such that the bottom surface of the feet contacts the skin of the patient at an acute angle designated as 102 and 102' where the angle is less than 90°, preferably of from about 10° to about 70°. The feet may be as wide as one side of the dressing or as narrow as about 5% of one side of the dressing. The hinges are made of soft, pliable polymeric material or a woven or non-woven fabric to allow easy movement of the dressing held loosely in place by the feet.

The feet are preferably covered with a pressure sensitive adhesive for attachment of the dressing to the skin of the patient. The pressure exerted on the top of the dressing 81 by environmental sources, such as clothing, is diverted onto the feet which, by their orientation due to the acute angle, will exert wound closing forces towards the center of the wound. Optionally, the dressing 80 may include straps 82, 82', 84, 84' which may be coated with a pressure sensitive adhesive on the skin contacting side thereof, or the straps may terminate into Velcro fasteners or buckles designated by 86, 86', 88, 88'. Contrary to the present invention, the prior art devices with fixed, vertical feed exert stretching forces on the skin around the wound which tend to open the wound.

The wound closing pressure of this embodiment of the present invention aids the healing process of the wound.

Figure 5A:
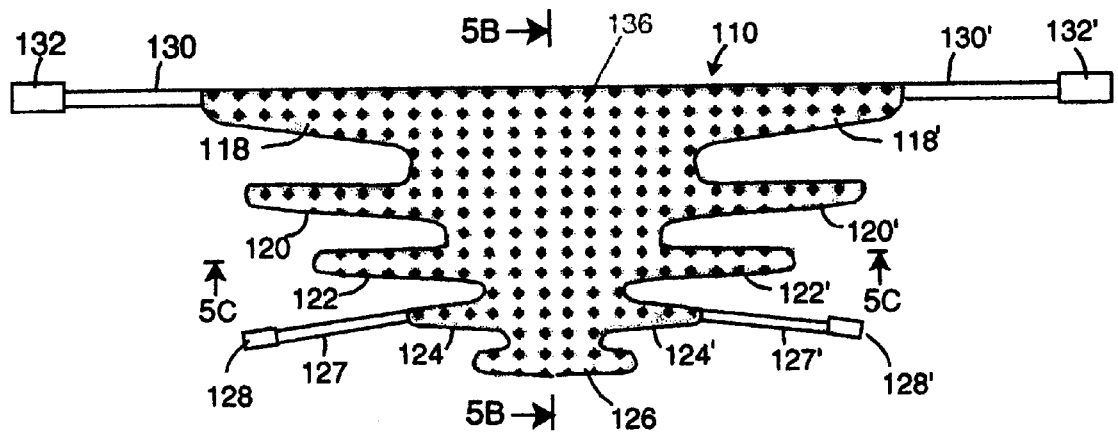
FIG. 5A is a top plan view of still another embodiment of the present invention.
Figure 5B:
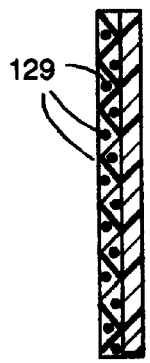
FIG. 5B is a cross-section thereof taken along the line of 5B—5B of FIG. 5A.
Figure 5C:
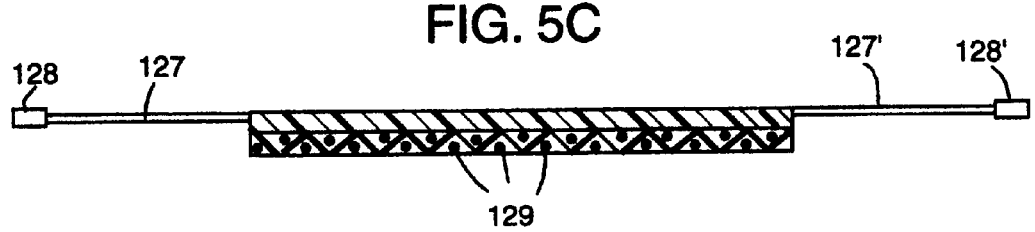
FIG. 5C is a cross-section thereof taken along the line of 5C—5C of FIG. 5A.

FIGS. 5A, 5B and 5C show another embodiment of the present invention wherein the dressing contains slits allowing the dressing to flex simultaneously in two directions.

In FIG. 5A a top plan view of the dressing 110 is shown wherein the dressing comprises: top central portions having multiple finger-like extensions 118, 118', 120, 120', 122, 122', 124 and 124'. Central top portion having the multiple finger-like extensions extend into and terminate in lower central bottom portion 126. The finger-like extensions are spaced from each other having slits therebetween. The slits allow the dressing to flex simultaneously in two directions, namely, in the direction along the line 5B—5B and in the direction along the line 5C—5C.

FIG. 5B shows a cross-sectional view of the embodiment of the invention taken along the line 5B—5B of FIG. 5A.

FIG. 5C shows a cross-sectional view of the embodiment of the invention taken along line 5C—5C of FIG. 5A.

To hold the dressing in place on the wound and its surrounding skin area, straps 127, 127', 130 and 131' are used, coated with a pressure sensitive adhesive on their skin-contacting face. Alternatively, Velcro fasteners or buckles 128, 128', 132 and 132' may be used on the end portions of the straps.

The numeral 129 denotes an optional medical gauze optionally impregnated with a pharmaceutical.

This embodiment of the present invention is especially preferred for a wound to the abdomen, the side or back where the wound crosses the belt line. While FIG. 5 illustrates one configuration, various curved and flexible configurations are further contemplated to fit different parts of the human anatomy.

Figure 6A:
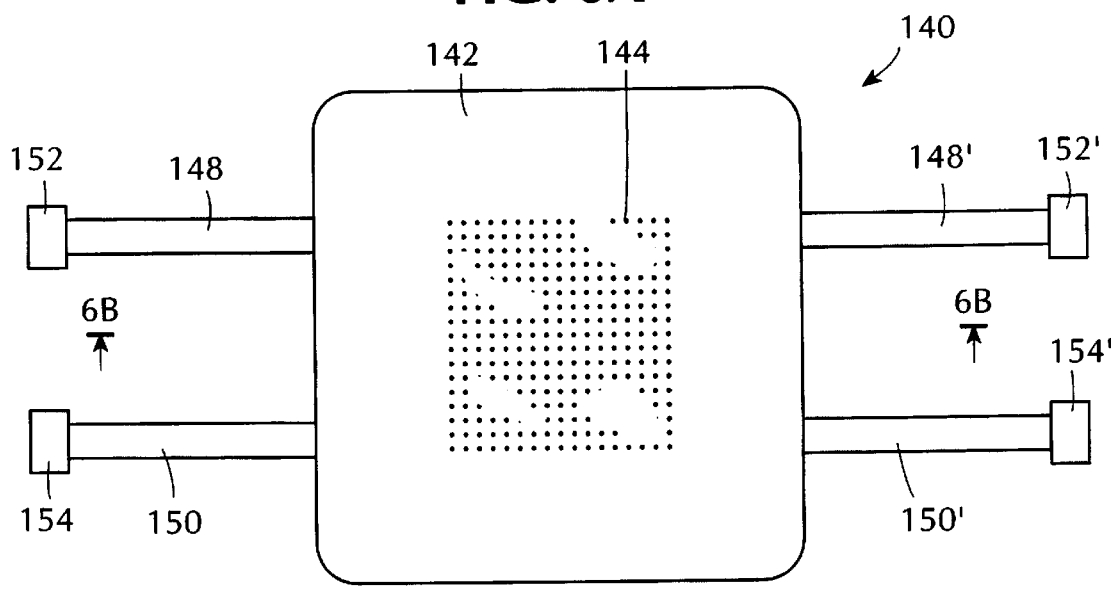
FIG. 6A is a top plan view of a further embodiment of the present invention.
Figure 6B:
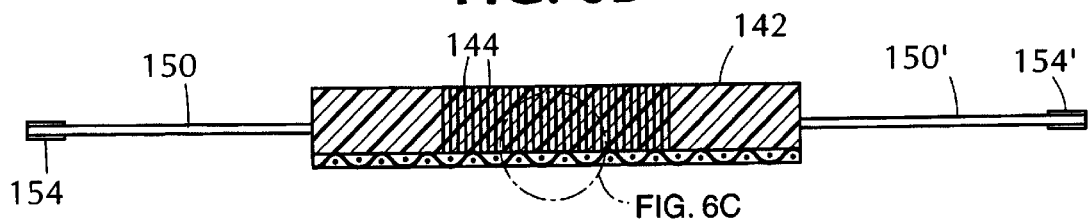
FIG. 6B is a cross-sectional view thereof taken along the line of 6B—6B of FIG. 6A.
Figure 6C:
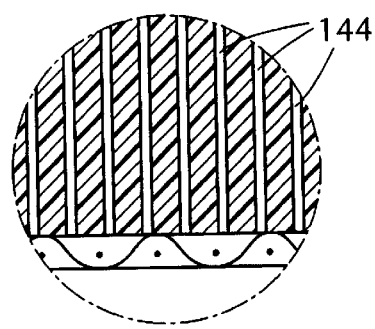
FIG. 6C is a greatly enlarged view of the portion shown in FIG. 6B designated FIG. 6C.

FIGS. 6A, 6B and 6C show another embodiment of the present invention in which the dressing contains a plurality of microscopic holes to allow the passage of air to the wound. As shown, the dressing 140 comprises a top portion 142, portions of which, preferably the center portion thereof, are provided with a plurality of microscopic holes 144. The holes can be made by a laser device well-known in the art or by piercing the device with a sharp needle-like instrument. The dressing 140 further comprises: straps 148, 148', 150 and 150' which are coated on their skin contacting side with a pressure sensitive adhesive for attachment of the dressing to the patient. Alternatively, the attachment means can be a Velcro fastener or a buckle designated by the numerals 152, 152', 154 and 154'. FIG. 6C shows a greatly enlarged portion of the dressing shown in cross-section in FIG. 6B, designated by "FIG. 6C", illustrating the microscopic holes in the dressing. The materials of construction are the same as in the previously described embodiments of the present invention.

Figure 7A:
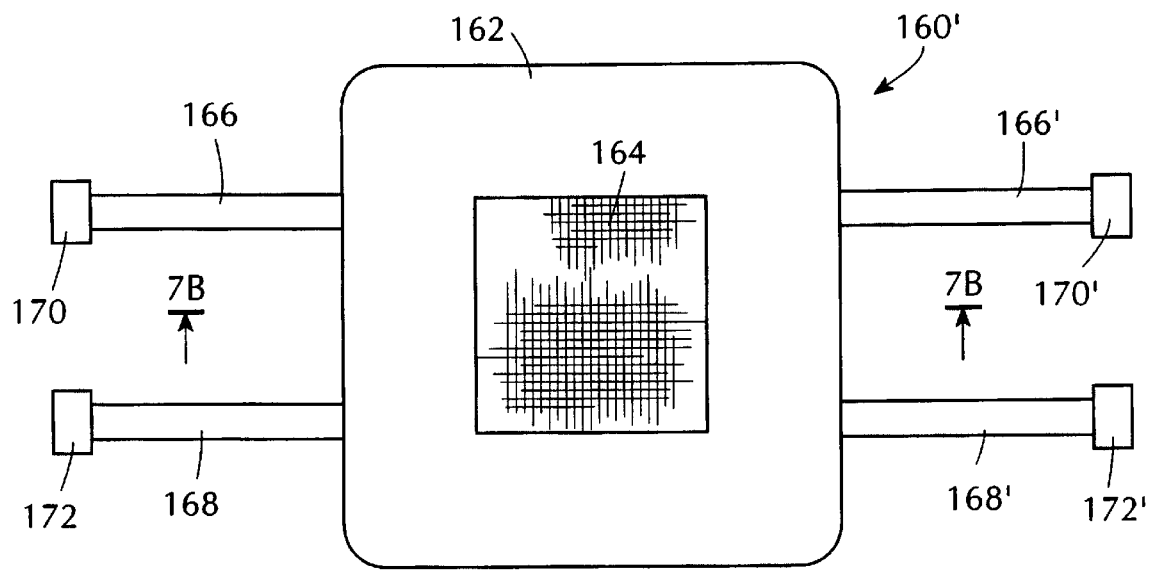
FIG. 7A is a top plan view of still another embodiment of the present invention.
Figure 7B:
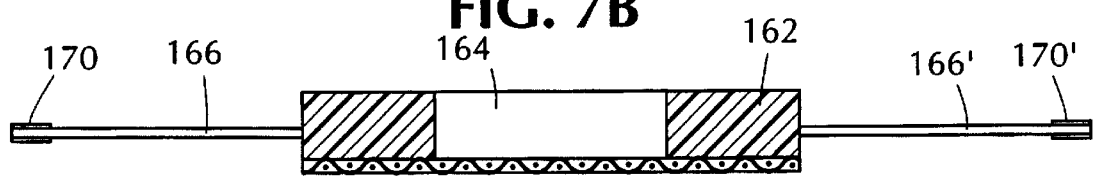
FIG. 7B is a cross-sectional view thereof taken along the line of 7B—7B of FIG. 7A.

FIGS. 7A and 7B show another embodiment of the present invention which allows more air to contact the underlying wound than the embodiment described in FIGS. 6A, 6B and 6C. The dressing 160' comprises: a top portion 162 enclosing a hole 164 in the center portion thereof. The hole may optionally be covered with medical gauze. The dressing further comprises: straps 166, 166', 168 and 168' coated with an adhesive on the underside thereof for attachment to the patient's skin. Alternatively, the straps without pressure sensitive adhesive coating may be equipped with Velcro fasteners or buckles 170, 170', 172 and 172'. The thickness of the dressing is at least $1/16$ inches and preferably greater than or equal to $1/8$ inches, but less than $1/2$ inch. The dressing is suitable for protecting the wound against broad, unfocused pressure, such as created by the trousers at the waist or a bra. The dressing will not protect against a small focused pressure smaller than the size of the hole in the center portion of the dressing.

Ingredients which contribute to the healing of the site of injury by preventing infection and accelerating the healing process may be used in the woven or non-woven material on the wound-contacting side of the semi-rigid, flexible sheet or pad of the device. Such ingredients are well known to those skilled in the art of healing and include antibacterials, antivirals, antifungals, anti-inflammatories, anesthetics, analgesics, antipruritics and mixtures thereof. These ingredients are described by the various editions of the Physicians Desk Reference (such as PDR, 1993 Edition) and are incorporated herein by reference. Non-limiting, illustrative examples are:

Antibacterial agents, such as Streptomycin, Rifamycin, Ampicillin, Penicillin O, Penicillin V, Bacitracin, Doxycycline, Methacycline, Minocycline, Tetracycline, Acetyl Sulfisoxazole, Succinylsulfathiazole, Sulfaloxic Acid, Sulfapyrazine, and Acetosulfone.

Antifungal agents, such as Dermostatin, Fungichromin, Clotrimazole, Econazole, Potassium Iodide and Propionic Acid.

Anti-inflammatory agents, such as Diclofenac, Tolmetin, Ibuprofen, Protizinic Acid, Glycol Salicylate and Sulfasalazine.

Antiseptic agents, such as Chlorhexidine, Calcium Iodate, iodine, Chloroxyelnol, Hexachlorophene, Boric Acid, and Cupric Sulfate.

Antiviral Agents, such as Acyclovir, Trifluridine and Ziovudine.

The invention has been described in detail with particular reference to certain preferred embodiments thereof, but it will be understood that variations and modifications can be effected within the spirit and scope of the invention.

What is claimed is:

1. A device for protecting a wound without exerting wound opening pressures on the wound comprising:

a flexible, semi-rigid flat dressing portion of rectangular, circular or strip configuration adapted to contact a wound and conform thereto, said flat dressing portion being made of a metal or a polymeric material, wherein said metal has a thickness of from about $1/64$ to about $1/16$ inches, and wherein said polymeric material has a thickness of from about $1/32$ to about $1/4$ inches, said flat dressing portion containing a plurality of microscopic holes therein allowing for air permeability;

a soft woven or non-woven fabric covering the wound-contacting side of said flat dressing portion; and means for attaching the flat dressing portion to the skin of the patient around the wound.

2. The device of claim 1 wherein said woven or non-woven fabric is impregnated with a pharmaceutically active agent selected from the group consisting of antibacterials, antivirals, antifungals, anti-inflammatories, anesthetics, analgesics, antipruritics, and mixtures thereof.

3. The device of claim 1 wherein said woven fabric is medical gauze.

4. The device of claim 1 wherein said metal is aluminum.

5. The device of claim 1 wherein said polymeric material is polyethylene or polypropylene.

6. The device of claim 1 wherein said means for attaching the flexible, semi-rigid flat dressing portion to the skin of the patient comprises straps coated with a pressure sensitive adhesive on the skin contacting side thereof.

7. The device of claim 1 wherein said means for attaching the flexible, semi-rigid flat dressing portion to the skin of the patient comprises straps equipped with hook and loop fasteners.

8. The device of claim 1 wherein said means for attaching the flexible, semi-rigid flat dressing portion to the skin of the patient comprises straps equipped with buckles.

9. A device for protecting an incision wound and exerting slight wound closing pressures on said incision wound comprising:

a flat flexible plastic or thin metal plate containing a plurality of holes or slits to allow air permeation therethrough; and attaching means having feet with hinges thereon integral with said plate, said attaching means forming an acute angle of from about 10° to about 70° with said plate thereby creating slight horizontal pressures towards the center of a wound when said device is placed on the wound, wherein said feet are covered by a pressure sensitive adhesive on the skin-contacting side thereof for attachment to the skin of a patient and said hinges are of soft, pliable material to allow movement of said plate.

10. The device of claim 9 wherein said plate is covered with a woven or non-woven fabric on the wound contact side thereof.

11. The device of claims 10 wherein said woven or non-woven fabric is impregnated with a pharmacologically active agent selected from the group consisting of antibacterials, antivirals, antifungals, anti-inflammatories, anesthetics, analgesics, antipruritics, and mixtures thereof.

12. The device of claim 9 wherein said feet contain Velcro fasteners thereon.

13. The device of claim 9 wherein said feet contain buckles thereon.

14. A device for protecting a wound without exerting wound opening pressure on the wound comprising: a flat flexible plastic or thin metal plate having a central opening therein consisting of from about 5% to about 95% of the plate, said plate having a thickness of from about $1/16$ to about $1/4$ inches.

15. The device of claim 14 wherein said central opening is covered with a woven or non-woven fabric on the wound contacting side thereof.

16. The device of claim 15 wherein said woven or non-woven fabric is impregnated with a pharmacologically active agent selected from the group consisting of antibacterials, antivirals, antifungals, anti-inflammatories, anesthetics, analgesics, antipruritics, and mixtures thereof.

17. The device of claim 14 further comprising, as integral parts of the device, attachment means selected from the group consisting of: straps coated with pressure sensitive adhesive on the skin-contacting side thereof, Velcro fasteners and buckles.

* * * * *